US008782552B2

(12) United States Patent
Batman et al.

(10) Patent No.: US 8,782,552 B2
(45) Date of Patent: Jul. 15, 2014

(54) ACTIVE OVERLAY SYSTEM AND METHOD FOR ACCESSING AND MANIPULATING IMAGING DISPLAYS

(76) Inventors: Sinan Batman, Pittsford, NY (US); Richard Kiesel, Waterville Valley, NH (US)

( * ) Notice: Subject to any disclaimer, the term of this patent is extended or adjusted under 35 U.S.C. 154(b) by 335 days.

(21) Appl. No.: 13/131,621

(22) PCT Filed: Nov. 25, 2009

(86) PCT No.: PCT/US2009/065967
§ 371 (c)(1),
(2), (4) Date: May 27, 2011

(87) PCT Pub. No.: WO2010/062979
PCT Pub. Date: Jun. 3, 2010

(65) Prior Publication Data
US 2011/0234630 A1    Sep. 29, 2011

Related U.S. Application Data

(60) Provisional application No. 61/118,580, filed on Nov. 28, 2008.

(51) Int. Cl.
*G06F 3/048* (2013.01)
(52) U.S. Cl.
USPC ........................................ 715/780
(58) Field of Classification Search
None
See application file for complete search history.

(56) References Cited

U.S. PATENT DOCUMENTS

| 5,724,985 | A | 3/1998 | Snell et al. |
| 2002/0169487 | A1 | 11/2002 | Graindorge |
| 2004/0051710 | A1* | 3/2004 | Hara ........................... 345/419 |
| 2004/0151358 | A1* | 8/2004 | Yanagita et al. ............... 382/132 |
| 2004/0196314 | A1* | 10/2004 | Bhogal et al. .................. 345/780 |
| 2004/0246270 | A1* | 12/2004 | Krishnamurthy et al. ..... 345/634 |
| 2005/0041844 | A1 | 2/2005 | Yamanaka |

(Continued)

FOREIGN PATENT DOCUMENTS

| JP | 2002-034948 A | 2/2002 |
| JP | 2005-065944 A | 3/2005 |

(Continued)

OTHER PUBLICATIONS

Jun Abe, Office Action, Japanese Patent Application No. 2011-538696, Mar. 8, 2013, 5 pages, Japan.

(Continued)

*Primary Examiner* — William Bashore
*Assistant Examiner* — Rayeez Chowdhury
(74) *Attorney, Agent, or Firm* — Woods Oviatt Gilman LLP

(57) ABSTRACT

The present invention is directed in general to imaging technologies and more particularly to medical imaging and picture archiving and communication systems (PACS) having an image display wherein system features and functions are provided to a user via active overlays located over displayed images. A system and method are provided to imbed an ability to interact with an image by activating traditional annotations that are displayed in conjunction with an image in a PACS. Users are able to access program functionalities in an improved, quicker, accurate and more intuitive means. More specifically, the present invention relates to providing the capability to customize multiple context menus, and flatten the command hierarchy of an imaging system. The present invention also provides the ability to "overload" current text and graphic annotations that are already displayed within an image of interest.

18 Claims, 5 Drawing Sheets

(56) References Cited

U.S. PATENT DOCUMENTS

| | | | |
|---|---|---|---|
| 2005/0228250 A1* | 10/2005 | Bitter et al. | 600/407 |
| 2007/0057962 A1 | 3/2007 | Matsumoto | |
| 2008/0141117 A1 | 6/2008 | King et al. | |
| 2008/0141155 A1 | 6/2008 | Wierowski et al. | |
| 2010/0141675 A1 | 6/2010 | Matsumoto | |

FOREIGN PATENT DOCUMENTS

| | | |
|---|---|---|
| JP | 2005-287891 A | 10/2005 |
| JP | 2007-079960 A | 3/2007 |
| JP | 2007122230 | 5/2007 |
| JP | 2008059176 | 3/2008 |
| JP | 2008078937 | 4/2008 |
| WO | 2006036290 | 4/2006 |
| WO | WO 2008/060323 | 5/2008 |

OTHER PUBLICATIONS

Sommermeyer, K., "Declaration of Non-Establishment of International Search Report," mailed Sep. 6, 2010, for International App. No. PCT/US09/65967, Rijswijk, Netherlands.

Barba, M., "Written Opinion of the International Searching Authority," mailed Sep. 6, 2010, for International App. No. PCT/US09/65967, Rijswijk, Netherlands.

Inoue, Koji. "Switching, Upgrading, Restoring a Computer to Factory Settings . . . Recommendation of Backup for an Emergency, Perfect Technique for User Profile Backup—Practical Guide No. 1: Managing Multiple PCs with User Profiles," Windows Server World, Japan, IDG Japan Ltd., vol. 10(1), 2005, pp. 140-143.

Abe, Jun, "Notification of Reasons for Rejection," for Japanese Patent Application No. 2011-538696, mailed Dec. 13, 2013, Tokyo, Japan.

* cited by examiner

ACTIVE OVERLAY SYSTEM AND METHOD FOR ACCESSING AND MANIPULATING IMAGING DISPLAYS

CROSS-REFERENCE TO RELATED APPLICATIONS

This application is a National Stage filing under 35 U.S.C. §371 of International Application No. PCT/US2009/065967, filed Nov. 25, 2009, which in turn claims the benefit of U.S. Patent Application No. 61/118,580, filed Nov. 28, 2008, both of which are hereby incorporated by reference in their entirety.

FIELD OF THE INVENTION

The present invention is directed in general to imaging technologies and more particularly to medical imaging and picture archiving and communication systems (PACS) having an image display wherein system features and functions are provided to a user via active overlays located over displayed images. A system and method are provided to imbed active text and graphic annotations onto images that are displayed with a PACS, for enabling direct user interaction with the system and direct manipulation of display images. Users are able to access program functionalities in an improved, quicker, accurate and more intuitive manner.

BACKGROUND OF THE INVENTION

In medical imaging, PACS are a combination of computers and/or networks dedicated to the storage, retrieval, presentation and distribution of images. While images may be stored in a variety of formats, the most common format for image storage is Digital Imaging and Communications in Medicine (DICOM). DICOM is a standard in which radiographic images and associated meta-data are communicated to the PACS system from imaging modalities for interaction by end-user medical personnel.

PACS display textual and graphical medical information that are associated with image attributes. Some of this information is received from DICOM and others are generated within the PACS as annotations that are associated with the images or measurements linked to anatomical regions of interest or markers that are produced by third party systems, such as Computer Aided Detection (CAD) applications. The DICOM standard recently introduced support for Structured Reports (SR) that can include CAD findings and GSPS (Grayscale Soft Copy Presentation State) non-image objects that are necessary to reproduce the same visualization of an image if displayed at two disparate PACS systems. Not all annotations are covered under the GSPS umbrella and often these attributes are displayed as static image overlays that can be turned on or off, based on the viewer's preference.

For example, certain attributes that are related to image processing are displayed as numerical value annotations that are associated with the rendering of a particular image. Such rendering may include image rotations, contrast adjustments such as window-level operation, particular proprietary image enhancements, zooming level, image compression level, etc. Traditionally, an end-user is able to manipulate the attributes of an image utilizing keyboard short cuts, combinations of mouse and keyboard buttons and mouse movement, or by simply launching tool menus to image tiles, context menus (often launched using right mouse click) or tool bars. The usability of accessing functions through these interfaces and techniques is rather low and presents a number of problems to the end-user.

Access to tools, whether associated with visualization, diagnostic workflow or clinical context driven measurements, is rather poor in existing PACS products. In the case of the Context Menu, which is conventionally launched by right clicking the mouse, navigating down the command hierarchy, access to particular command is often difficult and interferes with the user's ability to perform functions in a quick and efficient manner. What is needed is an intuitive and quick access to the context menu commands and other commands and features of the PACS, without further cluttering the screen real estate. The ability to access tools using active overlays within the image area, as opposed to the existing menu and toolbar driven approaches, reduces the number of commands that need to be exercised from menus. This in turn makes the menus more tractable. The aforementioned deficiencies identified are clearly not restricted to context menu, toolbars and toolboxes alone. There is also the broader issue of how to better utilize existing mediums or products to facilitate efficiency, ease of use and accuracy.

There is a need for an efficient, scalable, user friendly and robust technique to enable direct manipulation of image visualization parameters, provide access to other image related records, and enable modification and addition to measurement parameters while also providing access to toolbars and toolboxes.

The present invention fills these needs as well as other needs.

SUMMARY OF THE INVENTION

The present invention is directed to active annotated image overlays and providing access to features and functions of an imaging review system. The present invention provides the ability to "overload" current text and graphic annotations that are already displayed within an image of interest. Some of these annotations may be missing from certain images due to non-compliant DICOM modalities or non-DICOM images in general. The present invention includes automated and semi-automated generation of these annotations and their subsequent overloading.

More specifically, the present invention provides visual shortcuts to program functions, direct access to other images or relational information, and rapid selection of preferred image slices.

Even further, the present invention provides quick access to predetermined and often utilized menu item selections, in response to the user hovering over a particular region of the image containing an overloaded static text or graphics overlay.

Further still, the present invention enables the modification of information pertaining to image visualization, the image object and image measurements, without the need to search for menu items, and be distracted from the image of interest.

BRIEF DESCRIPTION OF THE DRAWINGS

The above-mentioned and other features and advantages of this invention, and the manner of attaining them, will become apparent and be better understood by reference to the following description of the invention in conjunction with the accompanying drawings, wherein.

DETAILED DESCRIPTION OF THE INVENTION

Generally, the tools and methods described herein for creating and implementing the active overlays to access, manipulate, and otherwise interact with images may be implemented in hardware, software or a combination thereof.

This document is organized as follows. In the first section, an overview of the techniques and implementation as provided by an exemplary PACS are provided and described. In the next section, an exemplary implementation of the present invention to access and manipulate attributes of an image series displayed in a tile window is discussed. Following this, other aspects of the invention as they pertain to accessing other features of the PACS, including manipulating the image window and images are discussed, along with the operational function of the present invention. Finally, an exemplary computer environment for the implementation and use of the invention is described.

The present invention provides a system and methodology to imbed the ability for user interaction with images, within image annotations. Although the following discussion and the present invention are described in relation to a biological imaging system (i.e., PACS), it should be understood that the invention is also applicable to other information/imaging technologies and systems. Such systems include those wherein image manipulation, image attributes and features of an imaging system are required to be intuitively and easily accessible to users, including non-medical systems, visual analysis and diagnostic tools, and other visual user interface environments.

Figure 1:
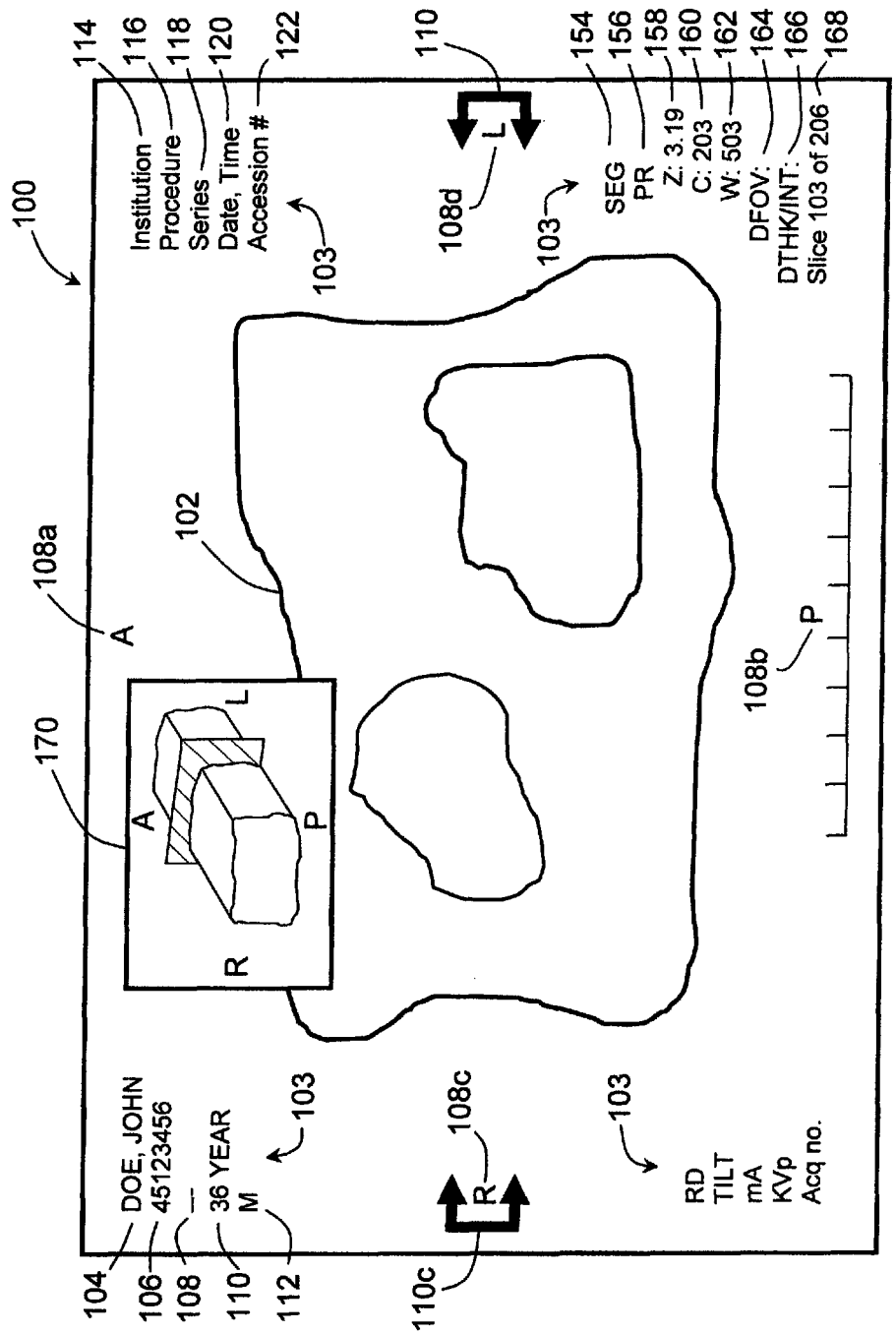
FIG. 1 is a block diagram illustrative of an image display in a PACS, to which the present invention would apply and be implemented.

FIG. 1 is a block diagram of an exemplary window of a PACS that illustrates an operational interface environment for application of the present invention. The illustrated window 100 represents a screen from a PACS, containing an image 102, along with various other information and annotations. The information and annotations are generally stored as meta-data associated with the image 102. Image 102 can include multi-spectral images, multi-modal (fusion) images, animations, or videos, and other textual clinical documents, such as radiology reports (structure or unstructured), lab results, pathology reports. The meta-data that is associated with image 102 can be thought of as belonging to three categories, namely: (1) information related to visualization of an image; (2) information related to the imaged object; and (3) measurements associated with the image.

Information related to visualization of an image includes such things as layout, pose (flip, rotation, pan, zoom), nature and position of artificial or assumed light (radiation, elasticity or sound among others) sources with respect to the imaged object(s), assumed light reflecting characteristics of imaged object(s), image rendering geometry and related characteristics (image thumbnail, key-image indicators, cut-plane location, slice thickness, frame rate, Maximum Intensity Projection, Volume rendering, MPR), color or gray-scale balance, color palette choice and association with image artifacts (Pixel or voxel value(s), velocities), segmentation map, specialized image processing parameters, field of view, framerate, image quality based on the level of data compression, quality of rendering (early ray tracing, empty space skipping), and level of image blending (PET-CT).

Information related to the imaged object includes name and location (monument name, person's name and unique id, body part, address and/or GPS coordinates of the image target), kind of image (X-ray, paysage, nature, family photo), date and time, link to and information about other related images and documents (letters, reports etc., Dicom Structured Reports, Dicom GSPS objects).

Measurements associated with the image include image histogram, optical density, region of interest size and boundaries (size of field associated with certain type of plantations, tumor sizes and boundaries, left ventricle size, ejection fraction ratio), velocity or flow rate (left ventricle ejection fraction, intravascular ultrasound based blood flow measurement, object tracking), pixel coordinates, image registration offset (PET/CT registration, offset between satellite and map views), pixel value, text or graphic annotations associated with regions of interest within the image (street name, Computer Aided Detection or Diagnosis findings, image number (if one of many in a stack of images), image based simulation (simulated placement of an orthopedic implant).

It is common that the meta-data associated with any of these three categories is displayed as static textual or graphical image overlays within dedicated applications designed to visualize the images, such as shown in the application window 100. As shown, static textual annotations 104 to 168, generally referred to herein as text annotations 103, and graphical annotation 170, overlay the image 102 and provide meta-data information to an end user. An end user of PACS needs to manipulate the image 102 or otherwise access both the displayed and other meta-data parameters and values. In general, the most relevant meta-data information is presented as an image annotation. The tools to modify or manipulate the values associated with these text annotations 103 exist within a specialized computer application and are made available to the user via functionalities within a toolbar, toolbox, keyboard shortcuts, mouse buttons and/or touch-screen device. However, the present invention circumvents this requirement and provides access to the tools, directly via the annotations 103 themselves.

Specifically and as shown in FIG. 1, the window 100 includes a number of annotative texts 103. These annotations 103 are shown in the drawing figures and described herein as having relative positions in the window 100 merely for illustrative and explanatory purposes only. As would be appreciated by one skilled in the art such text and or images may be located anywhere within the window 100. Suffice it to say that certain values and information that are relevant and useful to the end user are displayed as overlay annotations on the image 102. In the upper left corner of the screen a first grouping of textual annotations, identified in table 1 along with a description and label number may be displayed relative to the image 102.

TABLE 1

| Annotation Text | Description | Label |
|---|---|---|
| John Doe | (patient name) | 104 |
| 45123456 | (patient ID) | 106 |
| Feb. 7, 1957 | (birth date) | 108 |
| 42 YEAR | (age) | 110 |
| M | (gender) | 112 |

In the upper right corner of the window 100, a second grouping of textual annotations as identified in table 2 may be displayed.

TABLE 2

| Annotation Text | Description | Label |
| --- | --- | --- |
| Darien Diagnostic Imaging | (institution name) | 114 |
| MR | (procedure description) | 116 |
| Series Description | (series description) | 118 |
| Nov. 24, 1998 13:17 | (date, time) | 120 |
| 12345678 | (accession number) | 122 |
| — | (contrast/bolus agent) | 124 |
| Blank | (blank) | 126 |
| LOC: 32 | (slice location) | 128 |
| THK: 6 SP: 2 | (slice thickness, slice spacing) | 130 |
| HFS | (patient position) | 132 |

In the lower right corner of the window 100, a third grouping of textual annotations as identified in table 3 may be displayed.

TABLE 3

| Annotation Text | Description | Label |
| --- | --- | --- |
| 9-INCH GP | (coil type) | 134 |
| NEX: 0.75 | (Number of Excitations) | 136 |
| EC: 1 | (echo number) | 138 |
| GR | (scan sequence) | 140 |
| FA: 60 | (flip angle) | 142 |
| TR: 33.33 | (repetition time) | 144 |
| TE: 8 | (echo time) | 146 |
| AQM: 128\256 | (Acquisition Matrix) | 148 |
| Blank | (blank) | 150 |
| Page: 1 of 2 | (page number, total pages) | 152 |

In the lower right corner of the window 100, a second grouping of textual annotations as identified in table 3 may be displayed.

TABLE 4

| Annotation Text | Description | Label |
| --- | --- | --- |
| SEG: MPVR | (segment) | 154 |
| PR: | (preset) | 156 |
| Z: 3.19 | (zoom) (monitor res at 1152 × 864) | 158 |
| C: 203 | (window center) | 160 |
| W: 503 | (window width) | 162 |
| DFOV: X x Y cm | (Displayed Field of View in cm) | 164 |
| Blank | (lossy image compression ratio) | 166 |
| IM: 56 SE: 1 | (image number, series number) | 168 |

For the sake of brevity, and because the particulars of each of the annotated texts 103 is not critical to an understanding of the present invention, the details for each of the annotations 103 will not be discussed in detail herein. However, a few examples of the annotated texts 103 will be described to convey the concept, implementation and advantages of the present invention.

For example, the current zoom factor of the currently displayed image 102 is represented by the annotated text field Z 158 having a value of 3.19. The image positioning, represented by center annotated text C 160, and width annotated text field W 162 and having values of 203 and 503 respectively, represents the relative position of the image 102 within the window 100. As the view or position of the image 102 is manipulated, the text overlay fields 158, 160, 162 are updated with corresponding values.

As can be appreciated from the number of annotated texts 103, the numbers of other capabilities respecting the image 102 that fall into the aforementioned three categories of image related meta-data parameters, are rather large. As such it would be difficult for a user to navigate through icons, context menus, and through hierarchies to find the right command to achieve a desired function on an image 102. The use of dedicated hot keys has heretofore been the preferred way for advanced user to access the available functions. However, this approach has drawbacks of its own. The large number of commands along with environments that require simultaneous use of other input devices such as, dictation equipment or the use of low light levels to clearly view a keyboard make it difficult for a user to find the right short cut or hot key strokes. Attempts to overcome some of these shortcomings have included the use of backlit keyboard keys such as those designed for computer gamers. However, these solutions tend to introduce a level of light that can interfere with the required adaptation of receptors in the human eye and can impede the user's ability to properly do their job, such as in radiological image review.

For repetitive tasks that require expedient review and manipulation of a large number of images, the use of a right mouse-click context-menu, toolbar and toolbox becomes less efficient since the user needs to take the user's attention away from the actual image. This is especially true in environments that require the use of multiple input devices such as a dictation microphone, a canvas or a keyboard. The diverted attention result in context switching in the visual task and possibly interferes with the eye's innate ability to adapt to the light balance within the target images. In applications such as those involving visual target detection (mine detection, or screening of pathology images or of breast mammograms), such distractions may result in loss of concentration, which in turn may lead to catastrophic errors and/or diminished operator productivity.

The present invention introduces a number of concepts and a unique paradigm for accessing information, features and functions of a PACS in connection with image visualization, review and analysis. However, as would be appreciated by one skilled in the art, the invention may be applicable to other Image processing and implementations, the references and discussion provided herein are strictly for illustrative purposes and are not intended to limit the scope of the invention. The present invention is described with reference to an embodiment wherein access is provided to perform functions on medical images, by overloading the previously described text annotations 103 as well as graphic annotations 107 that are displayed within an image 102 of interest.

With continued reference to FIG. 1, the current invention converts static image overlays to active overlays thereby enabling direct manipulation of image visualization parameters, easy access to other records related to the image, modification and additions to existing measurement values, and direct access to relevant functionalities imbedded within toolbars and toolboxes. Since all annotations are not necessarily active any number of indicia may be provided to indicate an active element. One method to indicate that an element is active is to display a different font style, type and size. Active graphical overlays also provide a different indication such as, when hovering over the active overlay graphic (could be text as well) results in the active overlay flashing, vibrating or being encircled by a line etc. This indication of an active element may occur after a predetermined delay. This behavior is configurable by each user and can be muted globally or per overlay element. In another embodiment of the present invention, a "TAB" function is provided. The TAB function enables the display of all active overlays in an image tile one after another. In operation, the manipulation of the view, position or other attribute of the image 102 is accomplished by directly manipulating the displayed annotated image parameters, such as by editing the text overlay fields 158, 160, 162 of the earlier described scenario. The overlay fields 158, 160, 162 are presented as active overlays in the present invention.

Active overlay as used herein describes a new complex image based user interface. Depending on the operation to be performed, it incorporates different types of low-level user interaction. In the preferred embodiment of the present invention, the implemented prototype highlights a field when the mouse pointer is over the object or of interest. An edit box is then displayed for text input after the mouse is clicked or the object is otherwise selected. Provided that the text input is accepted, the affected field value is changed via the appropriate operation. Depending on the field, other types of user interaction and operations can be done. For example, the highlighting can be replaced with the placement of ticker lines and bold fonts to signal the selected field of interest.

In an embodiment of the present invention, the implementation of an active overlay occurs in various files. First, in order to make a field active, the field is flagged in the text overlay template. Second, the low level user interface must know the bounding rectangle of the field on the view. And third, in order to update the field value, the field property and operation must be available as a context menu, toolbar or toolbox option or other PACS operation.

In another embodiment of the present invention, when the user moves the mouse over any rectangle that is in the Active Field, that rectangle is highlighted in red (an arbitrary user configurable color or these fields can be indicated by increased line thickness and/or bold fonts). Nothing else occurs unless the user then clicks the left mouse button. When the user presses the left mouse button when over an active rectangle, an edit control is created and placed over this rectangle so that the text is exactly aligned. Editable text field even some graphical annotation can be associated with a dropdown list of preset choices that can be displayed in addition or in lieu of the text field making it easier for the user to select a preset value.

Direct manipulation of visualization parameters in this context means hovering over the active overlay area by means of a mouse, gesture, canvas or touch sensitive screen and selecting from the drop down menus (this may require a right mouse click after the area becomes active following a pause threshold) or directly editing the text fields based on the annotation context (this may require a mouse click on the text portion of after the overlay becomes active). Easy access to other records, for example, may include the use of the date overlay field 120 to display a list of historical and related images or documents upon activation. This list can be in the form of thumbnails or a timeline. The active overlay may then enable the operator to select a subset of historical studies and display the studies next to each other according to a user specified layout.

Thus, each of the annotated texts 103 and the annotated graphics 170 are active fields that overlay the image 102. In other words, when the user, utilizing a mouse or other pointing device, hovers over the annotated text 103 or graphics 107, a user interface hint is provided and the click of a mouse button will result in an action or response by the PACS. In operation, for any field that is designated as active, bold fonts and grid lines or color may be used to differentiate between the active and regular overlays. The active overlays are preferably customizable by user on a roaming profile basis in a computer network.

In the preferred embodiment of the present invention, a user is able to interact with the image 102, by utilizing the active annotations 103, 107. In effect, this allows a user, in the case of the previously described image positioning values, to not just read static numeric values, but to actually hover over and click the requisite values C 160 or W 162 and edit the entries, thereby manipulating the window/level of the image 102. This operation is in sharp contrast to manipulating the window/level by using the mouse or hunting for the appropriate menu context and command to adjust the image 102. An advantage of the present invention is that it also allows the user to reach a desired value directly, instead of trying to adjust to reach a desired value via mouse movements, which are less precise when an exact window/level value is desired. For example, in a situation where a user needs to have the same level of magnification (Zoom) in order to more accurately compare multiple images, the ability to provide a precise value greatly simplifies and expedites the process.

In a further embodiment of the present invention, a user may hover over an active overlay such as a CAD marker and be presented with a menu from which a selection can be made for an appropriate workflow action.

In an even further embodiment, the present invention provides the ability to activate the Anterior (A) 108a, Posterior (P) 108b, Right (R) 108c and Left (L) 108d markers, which are typically displayed to indicate the direction of an X-ray imaging procedure. The activated markers 108 of the present invention enable a user to flip the image 102 as desired. Selection of the A 108a, or P 108b markers would flip the image 102 around a vertical axis, while selection of the R 108c, or L 108d markers would flip the image around a horizontal axis. Further still, hovering over any of these markers 108, would display activated overlay double headed arrows 110. Clicking or otherwise selecting one head of arrow 110 would rotate the image 102 ninety degrees in the corresponding direction of the user selected arrow 110 head.

In yet another embodiment the, present invention provides a mechanism whereby a slice number 164, may be edited to allow a direct jump to a specified slice in a stack of images, thereby eliminating any sequential pagination to reach the desired slice. A drop down menu may also be displayed to enable the user to jump to a particular anatomy or to the bottom or top of a stack.

In a further embodiment, when editing of the zoom Z field 158, clicking on the active overlay or hovering over the field displays a drop down list of pre-configured selections such as, 0.5*True size, 2*True size; etc. This enables a form of 'shortcut' to a desired zoom level or factor.

In an even further embodiment, user inputs into active overlay fields are validated against bounds for the current filed property. When a provided entry is out of bounds, the image remains unmodified and the active field reverts to the previous valid entry.

To further illustrate the features and benefits of the present invention, a screen shot of a window as displayed in a PACS depicting an image of a gated thorax abdominal aorta is next described with reference to FIG. 2. As shown, the window 200 includes various text annotations 203 and informational items that are presented to a user, along with a graphical annotation 270. The image 200 and annotations 203, 270 are consistent with those shown and earlier described with reference to FIG. 1 and are similarly labeled. A different prefix number is used in the labeling of each figure merely to indicate the relevant drawing figure. For example, the zoom field of FIG. 1 is identified as 158, and the zoom field of screen shot of FIG. 2 is identified as 258.

Figure 2A:
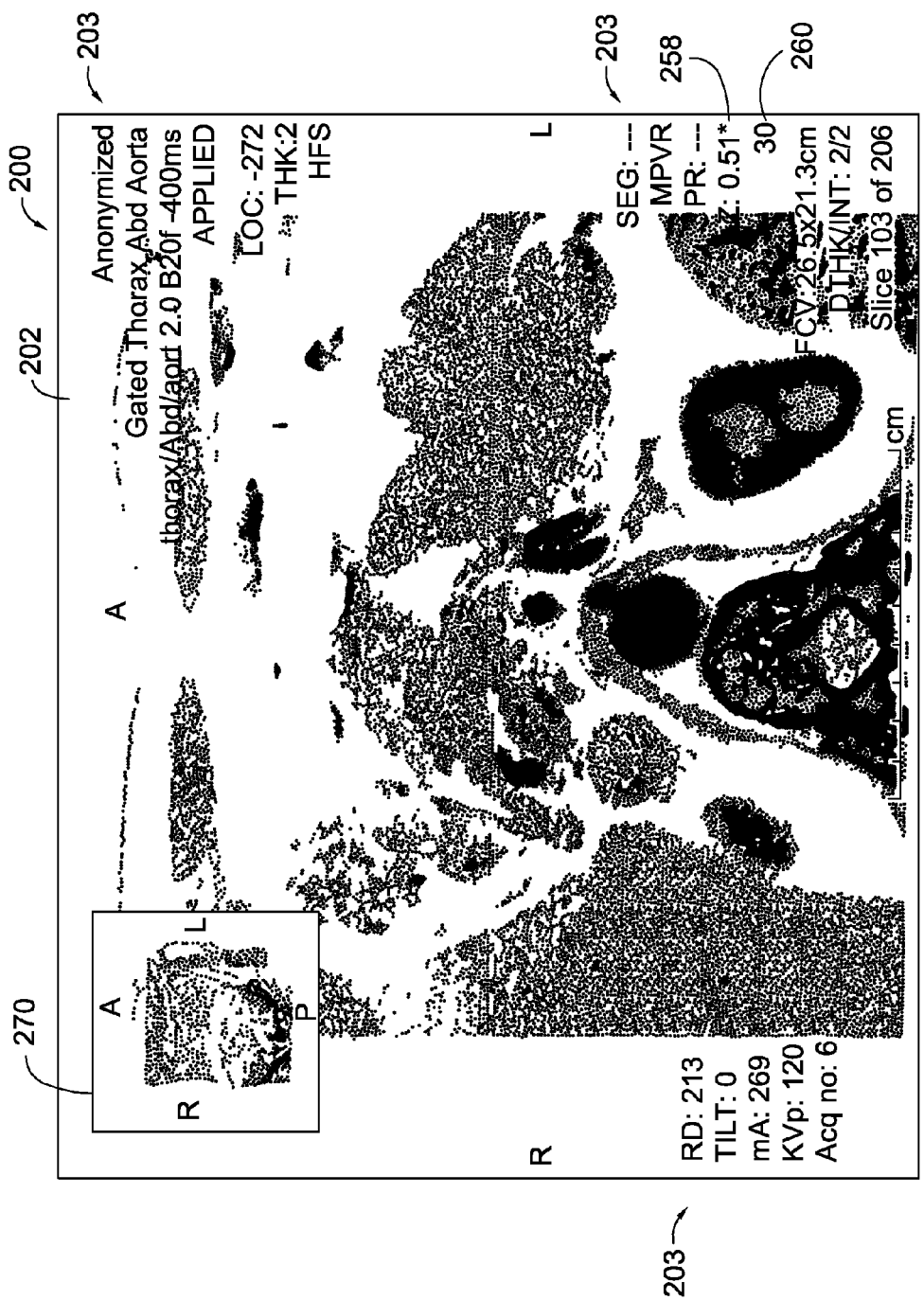
FIG. 2A is a screen shot of a window as displayed by a PACS showing an image along with the various text and informational items that are presented to a user.

The graphical annotation 270 illustrates an entire subject region and the location of the slice that is currently displayed as image 202. Of particular interest in FIG. 2A, is the center field 260, which is shown in a red box. This view is representative of a user having hovered over the center field 260. As previously described, the outlining of the field 260 provides an indication to the user that the field is an active field that is responsive to a click or other selection by the user.

Figure 2B:
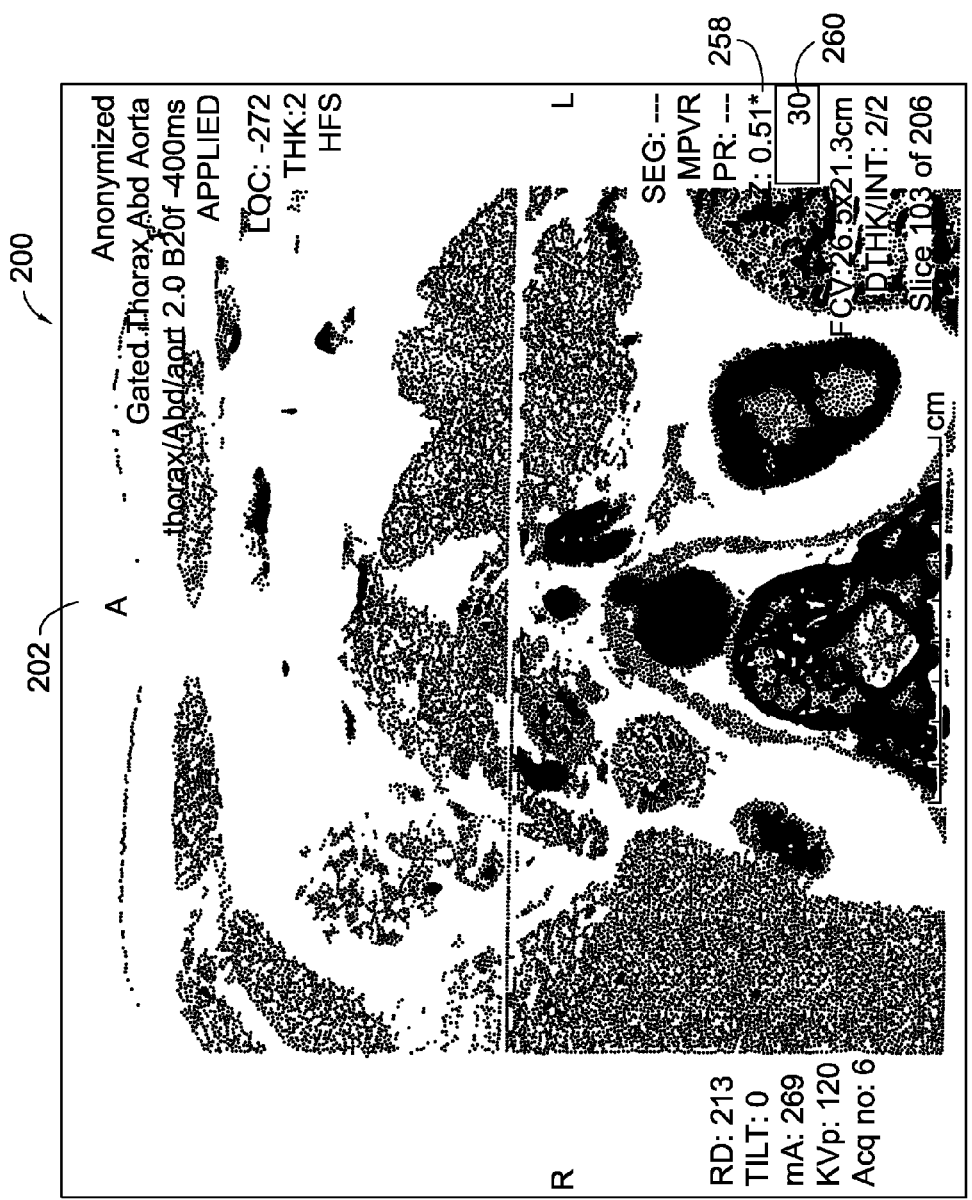
FIG. 2B is a screen shot of the window of FIG. 2, wherein the user has selected an active field and a text edit is displayed.

When the field 260 is selected, a text edit is displayed as shown in FIG. 2B. Notably, all of the text, i.e. "30", is selected so that user can immediately start typing a new value. As previously described, the newly typed value is bound checked and if accepted would result in an appropriate modification of the image 202.

Figure 3:
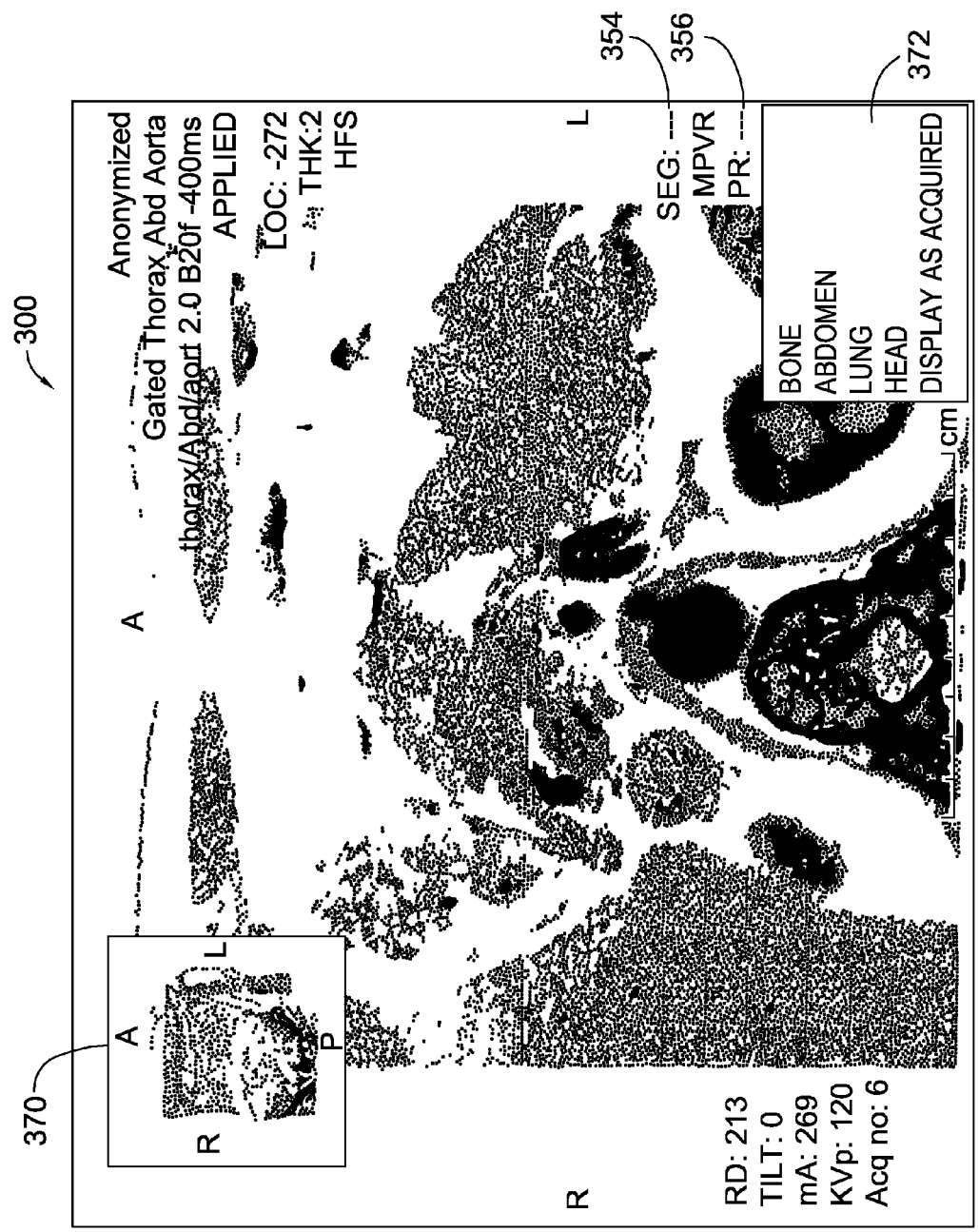
FIG. 3 is a screen shot of the window of FIG. 2, wherein the user has hovered over another active field causing the value to be highlighted and available values selections are displayed in a dropdown list.

In FIG. 3, a slight variation results from the selection of a different type of an active field, namely the preset field 356. As with FIGS. 2A and 2B, the image 300 and annotations are consistent with those shown and earlier described with reference to FIG. 1 and are similarly labeled. A different prefix number is used in the labeling merely to indicate the relevant drawing figure. For example, the SEG field 154 of FIG. 1, and the SEG field 354 of screen shot of FIG. 3 refer to the same field in a different view. As shown in the screen shot of the window of FIG. 3, when the user hovered over the active preset field PR 356, the value is highlighted and available values selections are displayed in a dropdown list 372 below the PR field 356 rather than highlighting the field. This option provides the user an alternative method of providing a new parameter as opposed to typing one in. The list 372 allows the user to select from one of Bone, Abdomen, Lung, Head, or Display as acquired.

Having described the system and method of the present invention and an embodiment thereof, an exemplary computer environment for implementing the described design and execution is presented next.

Figure 4:
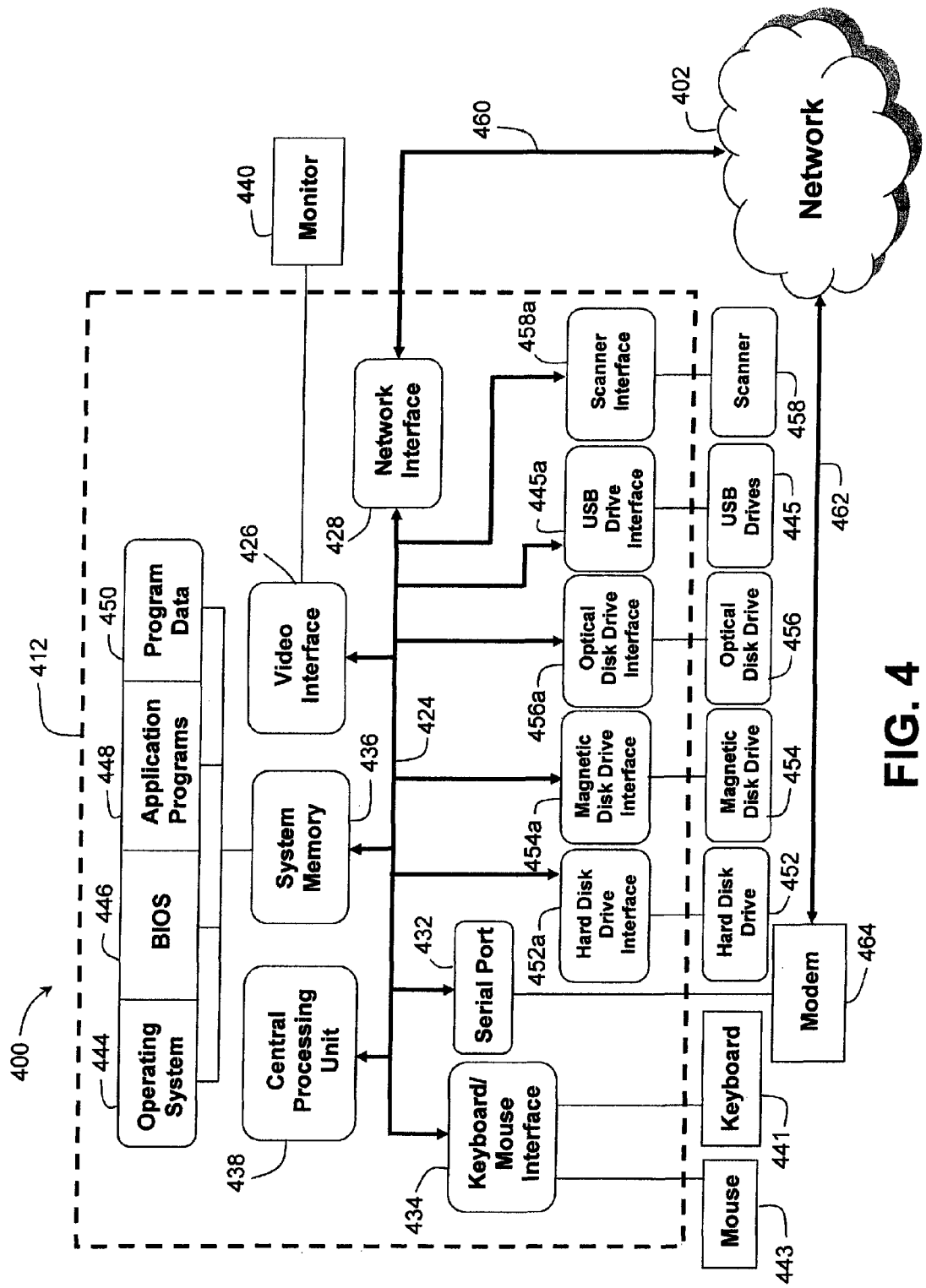
FIG. 4 is a block diagram generally illustrating a computing environment in which the invention may be implemented.

FIG. 4 shows an exemplary computing environment 400 that can be used to implement any of the processing thus far described. The computing environment 400 may comprise a computer 412 including a system bus 424 that couples a video interface 426, network interface 428, one or more serial ports 432, a keyboard/mouse interface 434, and a system memory 436 to a Central Processing Unit (CPU) 438. Computer 412 may also include a Graphics Processing Unit (GPU) or one or more other special or general purpose processing units. A monitor or display 440 is connected to bus 424 by video interface 426 and provides the user with a graphical user interface to view, edit, and otherwise manipulate digital images. The graphical user interface allows the user to enter commands and information into computer 412 using a keyboard 441 and a user interface selection device 443, such as a mouse or other pointing device. Keyboard 441 and user interface selection device are connected to bus 424 through keyboard/mouse interface 434. The display 440 and user interface selection device 443 are used in combination to form the graphical user interface which allows the user to implement at least a portion of the present invention. Other peripheral devices may be connected to computer through serial port 432 or universal serial bus (USB) drives 445 to transfer information to and from computer 412. For example, CT scanners, X-ray devices and the like may be connected to computer 412 through serial port 432 or USB drives 445 so that data representative of a digitally represented still image or video may be downloaded to system memory 436 or another memory storage device associated with computer 412 to enable processes and functions in accordance with the present invention.

The system memory 436 is also connected to bus 424 and may include read only memory (ROM), random access memory (RAM), an operating system 444, a basic input/output system (BIOS) 446, application programs 448 and program data 450. The computer 412 may further include a hard disk drive 452 for reading from and writing to a hard disk, a magnetic disk drive 454 for reading from and writing to a removable magnetic disk (e.g., floppy disk), and an optical disk drive 46 for reading from and writing to a removable optical disk (e.g., CD ROM or other optical media). The computer 412 may also include USB drives 445 and other types of drives for reading from and writing to flash memory devices (e.g., compact flash, memory stick/PRO and DUO, SD card, multimedia card, smart media xD card), and a scanner 450 for scanning items such as still image photographs to be downloaded to computer 412. A hard disk interface 452a, magnetic disk drive interface 454a, a optical drive interface 456a, a USB drive interface 445a, and a scanner interface 458a operate to connect bus 424 to hard disk drive 452, magnetic disk drive 454, optical disk drive 456, USB drive 445 and a scanner 458, respectively. Each of these drive components and their associated computer-readable media may provide computer 412 with non-volatile storage of computer-readable instruction, program modules, data structures, application programs, an operating system, and other data for the computer 412. In addition, it will be understood that computer 412 may also utilize other types of computer-readable media in addition to those types set forth herein, such as digital video disks, random access memory, read only memory, other types of flash memory cards, magnetic cassettes, and the like.

Computer 412 may operate in a networked environment using logical connections with image capture devices such as MRI, CT scanners, Ultrasound, Positron Emission Tomography (PET) or X-ray devices. Network interface 428 provides a communication path 460 between bus 424 and network 402, which allows images to be communicated through network 402 from any of the previously identified imaging devices, and optionally saved in a memory, to the computer 412. This type of logical network connection is commonly used in conjunction with a local area network (LAN). Images may also be communicated from bus 424 through a communication path 462 to network 402 using serial port 432 and a modem 464. Using a modem connection between the computer 412 and imaging devices may be used in conjunction with a wide area network (WAN) or the internet. It will be appreciated that the network connections shown herein are merely exemplary, and it is within the scope of the present invention to use other types of network connections between computer 412 and any imaging devices including both wired and wireless connections.

The present invention provides a useful, novel and non-obvious means to enable access to context menu, keyboard short-cuts and mouse button/movement combination functionalities within a diagnostic workstation through the use of relevant annotations that have been historically displayed along-side images but did not provide any capability for user interaction. By making the annotations active, several advantages are provided to the user, not the least of which is that the user does not need to divert attention away from the image and by so doing can increase his/her productivity.

From the foregoing, it will be seen that this invention is one well adapted to attain all the ends and objects hereinabove set forth together with other advantages which are obvious and which are inherent to the method and apparatus. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A computer implemented method providing access to one or more features and functions of a software tool that is utilized for interacting with and manipulating a display of at least one digital image by overloading one or more static annotated fields which are displayed as informational text or graphic overlays on top of the at least one digital image that is displayed using active overlays, the method comprising:

providing one or more annotated fields in an active overlay, said active overlay being utilized as opposed to a static overlay placed on top of the at least one digital image, and wherein said one or more annotated fields correlate to one or more image informational items and provide for the display of the one or more image informational items on the at least one digital image;

said one or more image informational items comprising at least one of parameters or values relating to the one or more features and functions of the software tool that interact with and manipulate the underlying display of the at least one digital image;

activating one or more of said annotated fields, wherein said activated annotated fields are configured for accepting direct input of an entry related to said correlated one or more informational items;

wherein the movement of a cursor over said activated annotated fields provides an indicia to an end user that said activated annotated fields can accept direct input of said entry; and utilizing said entry to directly provide data to the one or more features and functions of the software tool to thereby interact with and manipulate the display of the at least one digital image, wherein the at least one digital image includes a radiology report.

2. A method in accordance with claim 1 wherein said entry provided to the one or more features and functions of the software tool provides a second display of a second digital image, wherein said second digital image is related to the display of the digital images.

3. A method in accordance with claim 1 wherein said entry provided to the one or more features and functions of the software tool provides display of documents related to the display of the at least one digital image.

4. A method in accordance with claim 1 wherein said entry provided to the one or more features and functions of the software tool circumvents shortcuts to software menu items of the software tool for providing access to other images, relational information, or selections of the at least one digital image.

5. A method in accordance with claim 1 wherein the at least one digital image further includes a multi-spectral image.

6. A method in accordance with claim 1 wherein said one or more annotated fields provided in said active overlay are specified by an end user.

7. A method in accordance with claim 6 wherein said one or more informational items are stored as meta-data associated with the at least one digital image.

8. A method in accordance with claim 1 wherein activation of said one or more annotated fields are customizable by an end user.

9. A method in accordance with claim 1 wherein said inputted entry is utilized to manipulate image visualization parameters.

10. A method in accordance with claim 1, further comprising providing bounds checking on said inputted entry.

11. A method in accordance with claim 10, further comprising utilizing said inputted entry to provide data to the one or more functions of the software tool and thereby access features of the software tool.

12. A method in accordance with claim 1 wherein said indicia is mutable by an end user either globally or for each of said one or more annotated fields.

13. A method in accordance with claim 1 wherein activation is provided by overloading said one or more annotated fields.

14. A method in accordance with claim 1 wherein said active overlay is preferably customizable by an end user on a roaming profile basis in a computer network.

15. A method in accordance with claim 10 further comprising directing said inputted entry to provide toolbar choices or toolbox entries to thereby manipulate the visualization aspects of the at least one digital image.

16. A method in accordance with claim 1 wherein said feature and functions of said software tool is a context menu operation.

17. A method in accordance with claim 16 wherein said context menu operation is a zoom operation, and wherein a user specifies a zoom factor value for the at least one digital image.

18. A method in accordance with claim 1, further comprising displaying available entry selections in a dropdown list from which a new parameter is selectable for said activated annotated fields that support entries.

* * * * *